US006630432B2

(12) United States Patent
Farrell et al.

(10) Patent No.: US 6,630,432 B2
(45) Date of Patent: Oct. 7, 2003

(54) PROCESSABLE SOAP BASED BARS COMPRISING SOAPS OF α HYDROXY ACID AND MINIMUM AMOUNT OF FREE FATTY ACID AND/OR MONOGLYCERIDE

(75) Inventors: Terence James Farrell, Tenafly, NJ (US); Charles Craig Nunn, Rutherford, NJ (US); Keith Francis, Clifton, NJ (US)

(73) Assignee: Unilever Home & Personal Care USA, division of Conopco, Greenwich, CT (US)

( * ) Notice: Subject to any disclaimer, the term of this patent is extended or adjusted under 35 U.S.C. 154(b) by 0 days.

(21) Appl. No.: 09/837,015

(22) Filed: Apr. 18, 2001

(65) Prior Publication Data

US 2002/0183218 A1 Dec. 5, 2002

(51) Int. Cl.$^7$ ........ A61K 7/50

(52) U.S. Cl. ........ 510/152; 510/153; 510/155; 510/141; 510/133

(58) Field of Search ........ 510/152, 153, 510/155, 141, 130

(56) References Cited

U.S. PATENT DOCUMENTS

| | | | | | |
|---|---|---|---|---|---|
| 1,487,552 | A | | 9/1974 | Johnston et al. | |
| 3,991,001 | A | | 11/1976 | Srinivasan et al. | |
| 4,268,424 | A | | 5/1981 | Hall et al. | |
| 4,765,922 | A | | 8/1988 | Contamin et al. | |
| 6,074,998 | A | * | 6/2000 | He et al. | 510/155 |
| 6,218,348 | B1 | * | 4/2001 | Aronson et al. | 510/153 |
| 6,255,265 | B1 | * | 7/2001 | Van Gunst et al. | 510/152 |

FOREIGN PATENT DOCUMENTS

| | | |
|---|---|---|
| GB | 2016507 | 9/1979 |
| GB | 2243615 | 11/1991 |
| JP | 83004079 | 1/1978 |
| JP | 62199699 | 9/1987 |
| JP | 07026299 | 5/1995 |
| JP | 09087687 | 3/1997 |
| WO | 95/02035 | 1/1995 |

* cited by examiner

*Primary Examiner*—Necholus Ogden
(74) *Attorney, Agent, or Firm*—Ronald A. Koatz

(57) ABSTRACT

The invention relates to compositions comprising soap which, when used with at least 3% monoglyceride and or free fatty acid, allows incorporation of desirable α-hydroxy while retaining good ploddability properties. In another embodiment, the invention relates to process for making such bars.

3 Claims, No Drawings

PROCESSABLE SOAP BASED BARS COMPRISING SOAPS OF α HYDROXY ACID AND MINIMUM AMOUNT OF FREE FATTY ACID AND/OR MONOGLYCERIDE

FIELD OF THE INVENTION

The present invention relates to bars comprising primarily fatty acid soap as cleansing agent (although relatively small levels of synthetic surfactant are permissible) which bars also contain salts of alpha-hydroxy acids (e.g., sodium lactate).

BACKGROUND

It is greatly desirable to incorporate salts of α-hydroxy acids (e.g., sodium lactate) into soap bar compositions. Sodium lactate, for example, is a molecule which is found in the skin and has humectant properties. Consumer research has identified that presence of such natural moisturizing factors in personal wash products has considerable consumer appeal, especially if associated with a benefit.

Incorporating such salts, which are generally strong electrolytes, into a soap bar, however, can create processing dilemmas. Since these molecules are strong electrolytes, for example, they may easily disrupt the liquid crystal phases of the soap matrix which binds the insoluble soaps together. Without these liquid crystal phases, soap cannot be extruded in any meaningful way.

Unexpectedly, applicants have now found that use of monoglycerides (especially glycerol monolaurate) and/or free fatty acid added to superfat the composition results in stabilization of liquid crystal phases such that a quality soap bar comprising high levels (2% to 15%, preferably 3% to 14%, more preferably 4% to 14% by wt.) of, for example, sodium lactate can be produced. While either superfattying free fatty acid or monoglycerides may be used in the absence of the other, there must be at least 3% by wt. of one, the other or both.

The use of certain moisturizing salts, e.g., lactates and glutamates, in soap based bars is not new. GB Patent 1,487,552 (assigned to Unilever) discloses at page 2, Example II, for example, tallow soap bars which may contain 12%, 15% or 18% sodium lactate. When attempts were made by applicants to extrude such bars, it was found to be extremely difficult (for example, 5 bars per hour or less versus at least 30 bars per hour which can be extruded using bar compositions of invention). This failure is not surprising because the previous patent specification does not teach or suggest use of monoglyceride and/or free fatty acid (and, as noted, minimum 3% of one, the other or combination of two). Thus, there is no recognition of the interaction of the salt with the monoglycerides and/or with free fatty acid and how this interaction leads to the high quality bars of the invention.

JP 83004079 discloses soap compositions comprising lactic acid, lauric acid condensate soap with fatty acid soap. Lactic acid is disclosed in condensation reaction but there is no disclosure of lactic acid or its salt in the final product. As such, there is no reason to believe there may or may not be processing problems and certainly no disclosure of additional components (e.g., monoglycerides and/or free fatty acid) to address these problems.

JP 62199699 discloses use of low levels (%) of lactic acid or sodium lactate to sodium soap base. There is no disclosure of adding ingredient (e.g., monoglycerides such as glycerol monolaurate and/or free fatty acid) to improve processing problems caused by the lactate salts.

JP 07026299 discloses composition comprising soap substrate, 5–50% anionic and/or amphoteric surfactant and mono fatty acid ester. The compositions of the invention comprise less than 10% by wt. synthetic surfactant, preferably less than 5%, more preferably 4% or less, more preferably 3% or less. Further, the Japanese reference does not appear to disclose salt of α-hydroxy acid or to recognize the synergy between the salt and monoglyceride which prevents the salt from affecting processing.

JP 0908767 discloses soap base, at least one clay mineral and at least one of several listed clays. There is no teaching or disclosure of monoglyceride or super-fattying agent and, although sodium lactate is disclosed in a laundry list of moisturizers, there is no teaching or suggestion of interaction of such with monoglyceride and/or free fatty acid.

SUMMARY OF THE INVENTION

Suddenly and unexpectedly, applicants have discovered there is an interaction between salt of α-hydroxy acid (e.g., sodium lactate) and monoglyceride and/or free fatty acid and that, because of said interaction, it is possible to make high quality, extrudable bars comprising said salt of α-hydroxy acid. That is, it is possible to make high quality soap-based bars comprising a desirable moisturizing agent.

More specifically, in one embodiment, the invention comprises a composition comprising:

(a) 40% to 80% by wt. fatty acid soap;

(b) 2% to 15% by wt. of a salt of α-hydroxy acid (e.g., sodium lactate);

(c) 0% to 15% by wt. monoglyceride (e.g., glycerol monolaurate);

(d) 0% to 15% by wt. free fatty acid; and (e) 7% to 25% by wt. water.

According to the invention and, while not wishing to be bound by theory, it is believed that the monoglyceride or free fatty acid ("superfat") or the combination of the two (there must be minimum 3% by wt. whether one alone is used or the combination is used) interact with salt α-hydroxy acid so that the salt does not disrupt liquid crystal phases of the soap matrix necessary for extrusion of a good "high quality" bar.

In a second embodiment, the invention comprises a method or process for making a ploddable bar containing α-hydroxy acid by mixing 40% to 80% fatty acid soap, 2 to 15% salt of α-hydroxy acid and water with at least 3% of monoglycerate, free fatty acid or mixtures thereof High quality product has been produced from neutralizing the appropriate fatty acids (e.g., using NaOH) and adding additional ingredients (e.g., glycerol monolaurate and sodium lactate), while molten; or blending alkalimetal lactate and GML to a preformed soap base.

DETAILED DESCRIPTION OF THE INVENTION

In one embodiment, the invention relates to a fatty acid soap composition comprising naturally moisturizing benefit agents such as salt of α-hydroxy acids (e.g., alkali metal lactate). Though these salts normally disrupt formation of liquid crystal phase and make bars extremely friable (e.g., readily crackable and extremely difficult to extrude), applicants have found that combination of monoglyceride (e.g., glycerol monolaurate), free fatty acid or both (although one may be present to exclusion of the other, at least 3% of one, the other or both is needed), allow high quality bars to be extruded. By high quality is meant a bar which can be extruded at least 25 bars per hour. In the absence of GML and/or free fatty acid at minimal levels, the material is uncohesive, powder-like and cannot be extruded.

In a second embodiment, the invention provides a process for making a ploddable bar (i.e., at rate of 25 bars per hour and greater) even where bar comprises relatively high levels of salts of alpha-hydroxy acids. The soap bars may be prepared by either neutralization or saponification. For example, ingredients are heated until molten (e.g., 80° C. or so) and a salt of alpha-hydroxy acid is added (most likely by means of a solution) to molten mixture. The molten mixture and salt combine readily and there is no time limit associated with this addition.

If fatty acid is to be used, it may be introduced into the mixture a number of ways. The fatty acids, for example, may be added directly to the mixer and melted. A second way to introduce fatty acid to the soap is to add an acid (e.g., citric acid) to react with the soap forming fatty acids. Third, if the soap was formed from a fatty acid neutralization, under neutralizing the fat charge can supply the required fatty material. A combination of any or all three of the described methods is also acceptable.

If a single chain length monoglyceride is to be sued, the material may be added to the mixer and molten or may be pre-molten and added to the mixer. If the salt of the alpha-hydroxy acid is in the form of a solution, the monoglyceride may be combined with the solution and then added to the mixer. If the soap base was prepared via saponification, then a fraction of the triglycerides may be partially neutralized yielding some monoglyceride.

The order of addition stated above is not meant in any way to limit the invention. The process is very robust and as long as the ingredients are blended for a sufficient period of time (e.g., 15 minutes at 80° C., not meant to be limiting) the material may be cooled, milled, extruded and subsequently pressed.

A second approach to combining the ingredients begins with using pre-formed soap noodles and mixing the ingredients well below the melting temperature of the soap (e.g., 35–50° C.). Pre-formed soap noodles may be added to a z-blade type mixer (or a similar type mixer which provides sufficient kneading action for blending the materials) and subsequently adding the salt of alpha-hydroxy acid, the fatty acid and monoglyceride as necessary, as described above. As long as the ingredients are mixed until homogeneous, the material may be cooled, milled, extruded and subsequently pressed.

The invention is defined in greater detail below.

Fatty Acid Soap

The present invention relates to compositions and process to make ploddable soap wherein compositions comprise 40% to 95%, preferably 50% to 80% by wt. fatty acid soap. By fatty acid soap is meant a $C_8$ to $C_{22}$ saturated or unsaturated, substituted or unsubstituted carboxylic acid soap. In another definition, soaps may be defined as alkali metal salts of natural or synthetic (alkanoic or alkenoic) acids having 8 to 22, preferably $C_{12}$ to $C_{24}$ carbons.

Still further, soap may be defined as salt of monocarboxylic acid using as cation sodium, potassium ammonium trialkanolamine (e.g., triethanolamine) and/or mixtures thereof. Preferably, the ratio of tallow to nut oil is 9:1 to 1:9 and iodine value (measure of unsaturation) is no greater than 60.

While it is preferred that synthetic surfactant like anionic, amphoteric, nonionic etc. be absent, it should be noted that use of small amounts, e.g., 0.1–20%, preferably less than 10%, more preferably less than 5% may be tolerated. Level of tolerance will depend on type of surfactant, if any, e.g., amphoterics are less tolerable generally than acyl isethionate.

Salt of α-Hydroxy Acid

A second requirement of the invention is that composition comprise 2% to 15% by wt., preferably 3 to 12% by wt. of a salt of hydroxy, (e.g., glycolic acid), more typically an α-hydroxy acid. Typically, such α-hydroxy acids includes lactic acid. Salt cations may include alkali metals such as sodium or potassium. Other salts of mono and dicarboxylic acids, such as tartaric, citric and malic are less desirable because high levels in soap bars tend towards efflorescence.

As noted previously and without wishing to be bound by theory, being a strong electrolyte the salt is believed to disrupt the liquid crystal phase of the soap matrix which binds the insoluble soaps together. When monoglyceride and/or free fatty acid are used, the liquid crystal phases are stabilized allowing a suitable product to be extruded.

Monoglyceride And/OR Superfat

A third requirement of the invention is that compositions comprise 0 to 15%, preferably 1 to 10%, more preferably 3 to 8% by wt. monoglyceride and 0 to 15%, by wt., preferably 2 to 10% by wt., more preferably 5 to 9% by wt. free fatty acid.

Although, as noted, one may be used without the other, there must be a -minimum amount of 3% of one, the other or both, preferably a combined total of 3% to 15%, more preferably 5% to 12% by wt.

The monoglyceride may be glyceryl monolaurate or glyceryl monostearate.

The fatty acid for superfattying may be obtained by adding fatty acid directly to the mixer, by under-neutralizing fatty acids used in preparing the soap or by adding a compound such as citric acid which reacts with the soap and thereby forms fatty acid and sodium citrate.

Water

Finally, water should be present in the compositions at levels of 7% to 20% by wt., preferably 9 to 16%; more preferably 10 to 13% by wt.

In addition to required ingredients noted above, compositions of invention may contain other optional ingredients well known in the art. Among these are included germicides, perfumes, colorants, fillers (e.g., talc, calcite, kaolin) etc.

Processing

The procedure for combining these materials is very flexible. One way of combining the ingredients is to weigh out a predetermined amount of soap noodles (formed from a conventional process by mixing ingredients, cooling and refining), warm and mix them to about 40° C., add the salt α-hydroxy acid (e.g., sodium lactate) followed by the monoglyceride (e.g., glycerol monolaurate). The monoglyceride can be added as either a solid or in molten form. The mass can then be milled and processed into bars. If superfatting is required instead of, or as well as monoglyceride, nut oil may be added to the mixer or citric acid may be added to react with some of the soap.

Another way of composing the formulation is to prepare the entire mass in a single pot under molten conditions. After the fat/oil has been neutralized, the salt of α-hydroxy acid and monoglyceride can then be added to the mixer. If super-fatting is required, the fat/oil can be under-neutralized or have nut oil or citric acid added to the mixer.

Therefore, the ingredients can be combined either to softened, preformed soap noodles or in the crutcher following the neutralization or saponification. Under-neutralizing oils can also lead to a supply of monoglycerides.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

In order to further illustrate the invention, the following examples were prepared using a range of tallow to nut oil soaps:

| | Wt. % | | | | | | | | | | |
|---|---|---|---|---|---|---|---|---|---|---|---|
| | Comparative 1 | Comparative 2 | 3 | 4 | 5 | 6 | 7 | 8 | 9 | 10 | 11 |
| 90:10 (Tallow/nut oil) | 77.0 | — | 73.5 | — | — | 72.0 | — | 69.5 | — | 67 | |
| 40:60 | — | — | — | 69.5 | — | — | — | — | — | | 71.5 |
| 10:90 | — | 77.0 | — | — | 69.5 | — | 72.0 | — | 69.5 | | |
| Glycerol monolaurate | — | — | — | — | — | 5.0 | 5.0 | 2.5 | 2.5 | | |
| Glyceryl monostearate | | | | | | | | | | 10 | 5 |
| Super-fat* | | | 7.5 | 7.5 | 7.5 | — | — | 5.0 | 5.0 | | |
| Water | 13.0 | 13.0 | 9.0 | 13.0 | 13.0 | 13.0 | 13.0 | 13.0 | 13.0 | 13.0 | 13.0 |
| Sodium lactate | 10.0 | 10.0 | 10.0 | 10.0 | 10.0 | 10.0 | 10.0 | 10.0 | 10.0 | 10.0 | 10.0 |
| Misc. qs. to 100% | | | | | | | | | | | |

*Super-fatting can be accomplished by either under-neutralizing the fats or adding nut-oil or citric acid after neutralizing the fat, during the mixing state.

By incorporating monoglycerides (i.e., glycerol monolaurate) and superfattying formulations, a stable "mortar" is formed which binds the material together and allows it to be readily extrudable (e.g., readily ploddable). In absence of these process aids (Comparatives 1 & 2), a friable material is produced which is nearly impossible to plod into billets.

Specifically, in Examples 1 and 2 (which did not contain monoglyceride and were not superfatted, the compositions could not be formed into billets under any conditions.

Examples 3 through 9 by contrast (and which did contain monoglyceride and/or superfat) were all passed through a two-stage, single screw extruder, formed into billets and pressed into bars. As tabulated above, a range of tallow to nut-oil soaps was investigated as well as the effects of super-fatting, incorporating monoglycerides and using combinations of the two.

Examples 3–9, which met conditions of the invention could all be extruded under same conditions as was 1 & 2 at a rate of at least 25 bars per hours.

Examples 10 and 11 show the monoglyceride is not intended to be limited.

Even though these examples do not include the use of non-soap surfactants, fillers, fragrances or other materials known within the art, these may still be regarded as being within the scope of the invention.

What is claimed is:

1. A fatty acid soap bar composition comprising:

(a) 40% to 90% by wt. soap;

(b) 2% to 15% by wt. salt of α-hydroxy acid;

(c) 1% to 15% by wt. monogyceride selected from the group consisting of glycerol monostearate and glycerol monolaurate;

(d) 0% to 15% by wt. free fatty acid; and (e) 7% to 25% by wt. water, wherein amount of (c) and (d) must comprise, alone or together, at least 3% of composition;

wherein said composition can be plodded at rate of 25 bars per hour or greater.

2. A composition according to claim 1, wherein α-hydroxy acid is alkali metal lactate.

3. A composition according to claim 1, comprising 3–8% of component (C).

* * * * *